United States Patent [19]

Witholt et al.

[11] Patent Number: 5,032,512

[45] Date of Patent: Jul. 16, 1991

[54] PROCESS FOR PRODUCING COMPOUNDS CONTAINING A TERMINAL HYDROXYL OR EPOXY GROUP AND MICROORGANISMS SUITABLE THEREFOR

[75] Inventors: Bernard Witholt, Hr Eeelde; Roland G. Lageveen, Gl Oroningwn, both of Netherlands

[73] Assignee: Rijksuniversiteit te Groningen, Broerstaat, Netherlands

[21] Appl. No.: 143,826

[22] Filed: Jan. 14, 1988

[30] Foreign Application Priority Data

Jan. 15, 1987 [NL] Netherlands ................. 8700085

[51] Int. Cl.$^5$ .......................................... C12P 17/02
[52] U.S. Cl. ........................... 435/123; 435/157; 435/172.3; 435/252.34; 435/281
[58] Field of Search ............ 935/14, 27, 38, 59, 935/60; 435/41, 58, 132, 155, 157–161, 172.3, 252.34, 320, 123, 281

[56] References Cited

U.S. PATENT DOCUMENTS 3,813,316 5/1974 Chakvabarty et al. ......... 935/59 X

FOREIGN PATENT DOCUMENTS 1189807 7/1985 Canada ............................ 435/132

OTHER PUBLICATIONS

Chakrabarty et al., 1971 *Genetics*, 68, No. 1, p. 510.
M. J. de Smet, A Biological Approach to the Synthesis of Epoxides, Thesis, 1982 Rijksuniversiteit Gronigen de Smet et al., *Enzyme Microb. Technol.* 5 (1983), pp. 352–360.
Witholt et al., *TIBtech,* 8, 46–52 (1990).
Chem. Abst. vol. 105, No. 3, No. 1979 6x (1986).
Chem. Abst. vol. 105, No. 1, No. 5162a (1986).

*Primary Examiner*—Richard A. Schwartz
*Attorney, Agent, or Firm*—Henry D. Coleman; R. Neil Sudol

[57] ABSTRACT

This invention relates to a process for the microbiological production of compounds containing a terminal hydroxyl or epoxy group from an aliphatic substrate or a substrate with an aliphatic side chain, using microorganisms genetically engineered so that they have retained their capacity to perform the terminal oxidation of the substrate, but are no longer able to convert the resulting oxidation product further to any significant extent. Preferred substrates are n-alkanes, n-alkenes, and n-alkadienes containing 6–12 carbon atoms. Preferred micro-organisms are genetically engineered *Pseudomonas oleovorans* and *Pseudomonas putida* strains lacking an active plasmidic alkanol-dehydrogenase gene. The invention also relates to micro-organisms thus genetically engineered.

12 Claims, 4 Drawing Sheets

PROCESS FOR PRODUCING COMPOUNDS CONTAINING A TERMINAL HYDROXYL OR EPOXY GROUP AND MICROORGANISMS SUITABLE THEREFOR

This invention relates to a process for producing compounds containing a terminal hydroxyl or epoxy group by culturing microorganisms resistant to the presence of bulk non-aqueous phases and having an alkane-hydroxylase enzyme system enabling them to perform a terminal oxidation of an aliphatic substrate or of an aliphatic side chain of a substrate, under aerobic conditions and in the presence of such a substrate, and recovering the oxidation product formed.

A similar process is described in the thesis "A Biotechnological Approach to the Synthesis of Epoxides" by M. J. de Smet (Groningen, 1982). As set out therein, some bacteria, such as *Pseudomonas oleovorans*, are capable of growing under aerobic conditions on different non-aromatic hydrocarbons, such as octane, octene, octanol, etc. *Pseudomonas oleovorans* can do this owing to a plasmid-coded mono-oxygenase system which catalyzes the first oxidation step in the decomposition of the hydrocarbon substrate. This mono-oxygenase, or rather in particular the alkane-hydroxylase system, which catalyzes hydroxylation of a terminal methyl group of n-alkanes and the conversion of terminal n-alkenes into the corresponding 1,1 oxides, consists of an ω-hydroxylase localized in the cytoplasmic membrane and having a molar weight of 41 kDa, an iron and sulphur containing cytoplasmic protein having a molar weight of 19 kDa (called rubredoxin) and a cytoplasmic flavoprotein with a molar weight of 55 kDa (called rubredoxin-reductase).

For bacteria to be able to grow on hydrocarbons, such as alkanes, they must be capable of converting the first oxidation product further. In *Pseudomonas oleovorans*, the n-alkanol is oxidized further, for this purpose, to an aldehyde which, in turn, is oxidized to a corresponding fatty acid, which subsequently is broken down further by β-oxidation. The conversion of alkanol into aldehyde is catalyzed, in *Pseudomonas oleovorans*, by alcohol dehydrogenase enzymes. The OCT plasmid of *P. oleovorans* contains, inter alia, genes coding for the alkane-hydroxylase system (alkBA genes), for an alcohol dehydrogenase (alkC gene), localized in the cytoplasmic membrane, and the regulation genes (alkR genes) necessary for their expression. The genes responsible for the further oxidation of the aldehyde to fatty acid and for the β-oxidation of the fatty acid, however, are located on the chromosome.

Bacteria such as P. oleovorans can be cultured in systems comprising two liquid phases, in which the bacteria themselves are contained in the aqueous phase and the substrate forms the non-aqueous phase, to produce the first reaction product consisting of n-alkanols and/or n-epoxyalkanes, according to the nature of the substrate. This possibility of a biocatalytic process was studied in the thesis by M. J. de Smet, referred to hereinbefore, including the possibility of producing compounds such as 1,2-epoxyoctane and 1,2-epoxydecane by culturing *P. oleovorans* in two-phase systems under aerobic conditions, using olefins such as n-octene and n-decene as a carbon source.

An important disadvantage of the production of alkanols carried out in this manner, however, is that the microorganism used converts the alkanol formed further, so that production is hampered. In the case of 1,2-epoxyalkanes formed from olefins, further breakdown is also possible, probably via a hydroxylation of the free methyl group.

The present invention provides a process which eliminates this drawback and is characterized by using microorganisms that have been genetically engineered so that they are still capable of performing the terminal oxidation of the substrate to a compound having a terminal hydroxyl or epoxy group, but are no longer able to convert the oxidation product further to any significant extent.

The nature of the substrate is closely related to the nature of the desired oxidation product. When, for example, n-octanol is the desired oxidation product, the substrate to be chosen will be n-octane. If it is desired to produce 1,2-epoxyoctane, the substrate to be taken will be n-octene. Depending on the nature of the substrate and the nature of the microorganisms used, in particular the specificity of the alkane-hydroxylase enzyme system thereof, the oxidation product will sometimes be a mixture of different compounds, for example, a mixture consisting of an 1,2-epoxyalkane and an alkenol when an olefin is used as the substrate. The nature of the microorganisms used and the alkane-hydroxylase enzyme system thereof is also determinative of the nature of the substrates that can be used.

Preferably, according to the invention, microorganisms of the species *Pseudomonas oleovorans* or of the species *Pseudomonas putida* are used, most preferably a microorganism of the species *Pseudomonas oleovorans*. Such microorganisms are by nature able to grow on n-alkanes and n-alkenes containing 6–12 carbon atoms, but the alkane-hydroxylase enzyme system thereof is also effective with other substrates, such as propene, butene, tetradecene, hexadecene, tetradecane, n-alkadienes containing 6–12 carbon atoms, n-alkanoic acids containing 6–12 carbon atoms, phenylalkanes, phenylalkenes, etc.

A preferred embodiment of the invention is characterized by using as the substrate one or more n-alkanes, n-alkenes and/or n-alkadienes containing 6–12 carbon atoms.

In principle, various kinds of genetic engineering can be used to reduce the capacity of the microorganisms to convert the first oxidation product further. Although microorganisms such as *P. oleovorans* contain several genes coding for alkanol-dehydrogenase, it has surprisingly been found that the deactivation or removal of the plasmid encoded alkanol-dehydrogenase gene (i.e., that located on a plasmid) results in a considerable deterioration of the bacterium's capacity to convert the first oxidation product further. Indeed, microorganisms with mutations in this plasmid encoded alkanol-dehydrogenase gene, which mutations may be site-directed and are sufficient to prevent the expression of this active alkanol-dehydrogenase enzyme, are examples of microorganisms suitable for use in the process according to this invention.

Microorganisms suitable for use in the process according to the invention can be obtained by using a host stripped of its natural plasmid, and providing it with a recombinant plasmid containing the alkBA/R genes coding for the alkane-hydroxylase system and not containing a gene coding for an active alkanol-dehydrogenase enzyme.

The natural OCT plasmid contains the required genes in the alk BAC operon positively regulated by the products of the alkR regulation genes. The alk BA genes coding for the alkane-hydroxylase enzyme system and the alkR regulation genes can be cloned in a suitable host, using a suitable vector system, e.g., pLAFRI vectors (Friedman et al Gene 18 (1982), 289–296). A suitable recombinant plasmid containing these alkBA and alkR genes and lacking the plasmidic alkanol-dehydrogenase gene alkC is the plasmid pGEc 41 based on pLAFRI.

An *E. coli* strain containing this plasmid pGEc 41 was deposited with the Centraalbureau voor Schimmelcultures at Baarn, The Netherlands, on Jan. 14, 1987 (*E. coli* DH1 (pGEc 41), CBS 102-87).

*Pseudomonas oleovorans* whose natural plasmid has been replaced by the plasmid pGEc 41 or a similar plasmid containing alkBA/R genes are no longer capable of growing on alkanes, alkenes and alkanols containing 6–12 carbon atoms, at least they grow significantly less well on such substrates than the wild-type bacteria. However, they are still resistant to the presence of bulk non-aqueous phases and as a consequence can be cultured in the presence of a nutrient medium with a suitable carbon source, such as pyruvate, citrate or glucose, in systems with two liquid phases, namely, an aqueous phase containing the bacteria and an organic phase, which may amount to as much as 99 % by volume without appreciable damage to the bacteria. For a good growth, it is recommendable for the pH of the system to be controlled at a value of between 5 and 9, preferably 6.8–7.0, and for the temperature to be controlled at a value below 37° C., preferably 20°–34° C., and most preferably 28°–32° C. To effect a good contact between the organic phase and the aqueous phase with bacteria and to effect good mixing and also decrease the risk of product inhibition without at the same time causing damage to the bacteria, the reactor contents are preferably continuously stirred at a stirring rate of 500–1000 rpm, or agitated otherwise to a comparable extent.

To minimize a negative effect of the product formed on the conversion of substrate as much as possible, a further preferred feature of the invention is that a second organic phase is used which removes the oxidation product formed from the aqueous phase more efficiently by virtue of a distribution coefficient for the product that is quite favourable relative to water. For this purpose, for example, cyclohexane, cyclohexanol, phthalic acid esters and diesters, such as dibutyl phthalate, have been found to be suitable. By adding, for example, dibutyl phthalate as a second organic phase in the microbiological production of octanol from octane by the process according to the invention, the ultimate product concentration can be doubled.

The invention is illustrated in and by the following experimental section.

1. Genetic engineering
   a. Bacterial starting strains
      The starting strains used for genetic engineering are listed in Table A.
   b. Media
      *E. coli* and *P. putida* were cultured on L medium or E* medium with a nutrient source (0.2% w/v) and required amino acids (0.01% w/v).

| | |
|---|---|
| L medium contains: | 5 g/l yeast extract |
| | 10 g/l bacto-trypton |
| | 10 g/l NaCl |
| | pH adjusted to 7.5 |
| E* medium contains: | 3.5 g/l NaNH$_4$HPO$_4$.4 H$_2$O |
| | 7.5 g/l K$_2$HPO$_4$.3 H$_2$O |
| | 3.7 g/l KH$_2$PO$_4$ |

After sterilization, 10 ml of a sterile 100 mM MgSO$_4$ solution and 1 ml of a trace elements solution, called 1000×MT were added. 1000×MT contains, per liter:

2.78 g FeSO$_4$.7H$_2$O
1.98 g MnCl$_2$.4H$_2$O
2.81 g CoSO$_4$.7H$_2$O 1.47 g CaCl$_2$.2H$_2$O
0.17 g CuCl$_2$.2H$_2$O
0.29 g ZnSO$_4$.7H$_2$O

For growth on octane, the strains were cultured on plates with E* medium with 1.5%(w/v) agarose at 32° C. in closed canisters with octane vapour. For selection for tetracycline resistance, this substance was added up to a concentration of 15 μg/ml.

c. DNA isolation
   Plasmid DNA of *E. coli* and *P. putida* was isolated by the method of H. C. Birnboim and J. Doly (Nucl.Acids Res. 7 (1979); 1513–1523).

d. Enzymes
   Restriction endonucleases, T4 DNA ligase and hen egg-white lysozyme were obtained from Boehringer Mannheim GmbH (Mannheim, Federal Republic of Germany) and Bethesda Research Labs GmbH (Neu Isenburg, Federal Republic of Germany). They were used in accordance with supplier's directions.

e. Mutagenesis of GPo-1'
   GPo-1 was cultured on L medium to a cell density of 0.1 mg/ml in a shaking water bath at 32° C. Nitrosoguanidine (NTG) was added to a final concentration of 50 μg/ml, and incubation was continued for another 30 minutes. The cells were subsequently centrifuged (5000 g, 5 minutes) and re-suspended in fresh L medium to a cell density of 0.05 μg/ml. Subsequently, the culture was incubated overnight at 32° C. and then diluted and plated on L-medium plates to produce isolated colonies. These were tested on E* medium with glucose, E* medium with octane vapour and on E* medium with octanol vapour.

Of the 3500 colonies found, 7 were no longer able to grow on octane but did grow on octanol, and these were studied further for the type of mutation. This showed that they had all lost the OCT plasmid. One of these 7 mutants was called GPo-12. When the OCT plasmid is re-introduced into this strain, the strain behaves as a normal GPo-1.

f. Genetic procedures
   The mobilization of pLAFRI of *E. coli* to *P. putida* was carried out by the "triparental mating" method described by Friedmann et al., Gene 16 (1982), 289–296. When the donor strain the recipient and the helper strain had been cultured overnight on an L plate, the exconjugants were selected by replica plating on plates with E* medium which also contained tetracycline, glucose and the required amino acids.

The transformation of *E. coli* with plasmid DNA was carried out by the method of Cohen et al. (Cohen SN, Chang AC and HSU L, Proc.Natl.Acad.Sci. 69 (1972), 2110–2114). In-vitro phage-Lambda packing extract was made and pLAFRI DNA was packed by the method of Hohn (Hohn, B in: R. Wu (ed), Methods in Enzymology 68 (1979), pp 299-309, Academic Press Inc., New York).

For transductions, *E. coli* HB 101 was used (Boyer et al.). It was cultured overnight in 5 ml L medium. The cells were next centrifuged and resuspended in 5 ml 10 mM MgSO$_4$ and so kept overnight. The next day these *E. coli* cells, which have been starved for a carbon and energy source were mixed with the correct amount of in-vitro packing cosmids and incubated at room temperature for 15 minutes. Thereafter 0.2 ml L medium was added and the cell suspension was incubated at 37° C. for 1 hour. Transductants of *E. coli* were then plated on an L plate with tetracycline.

g. Construction of strains pGEc29 (pLAFRI with 16.9 kb insert containing the alkBAC operon) and pGEc40 (pLAFRI with 18 kb insert containing the alkR locus) were ligated together in a 1:1 ratio after digestion with EcoRI. The ligation mix was packed in-vitro in phage lambda heads and HB101(*E. coli*) was transduced with this mix. To identify transductants, the material was selected for tetracycline resistance.

In this way, a plasmid (pGEc47) was obtained in *E. coli* HB 101 containing in pLAFRI both the 18 kb and the 16.9 kb inserts. In addition, a plasmid was obtained (pGEc41) containing the complete alkR locus and, from a spontaneous deletion, only a portion of the alkBAC operon, i.e., alkBA (see FIG. 3b). This plasmid accordingly lacks the plasmid-coded alkanol-dehydrogenase (alkC). See for genetic determinants of pGEc41 and pGEc47 Table C. Both plasmids pGEc41 and pGEc47 were introduced into *P. putida* and the plasmid-stripped *P. oleovorans* strain GPo-12 by conjugation (see under f). For growth characteristics, see Table B.

The employed vector pLAFRI (Tc, Tra, Mob, RK2 replicon) was described by Friedman et al., Gene 18 (1982), 289-296. All of the DNA fragments referred to were isolated from a gene library of the total *P. oleovorans* genome. This gene library was constructed by Eggink and described in: Innovations in Biotechnology (1984), Vol. 22, E. Houwink and R. R. van der Meer (eds.), pp 373-380.

Selection was effected by complementation, as set forth in Table C.

The plasmids pGEc 29, pGEc 40 and pGEc 47 were obtained by ligation with EcoRI digested pLAFRI.

Figure 1:
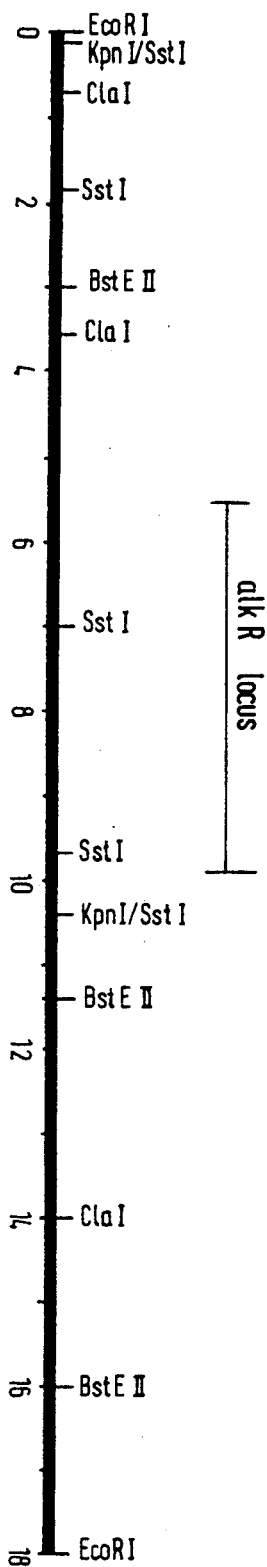
FIG. 1 illustrates the restriction chart of the EcoRI fragment B inserted into pGEc 40, which fragment contains the alkR locus.
Figure 2:
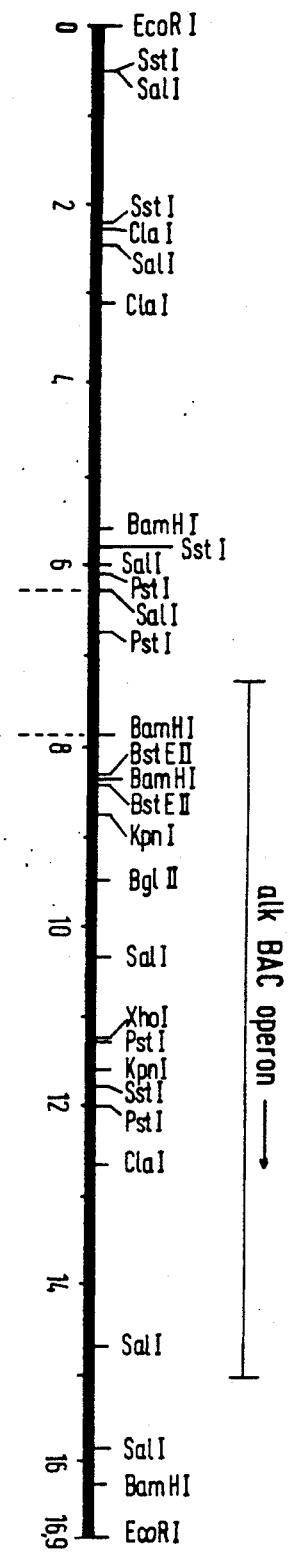
FIG. 2 shows the restriction chart of the EcoRI fragment A, containing the alkBAC operon, inserted into pGEc29.
Figures 3A, 3B:
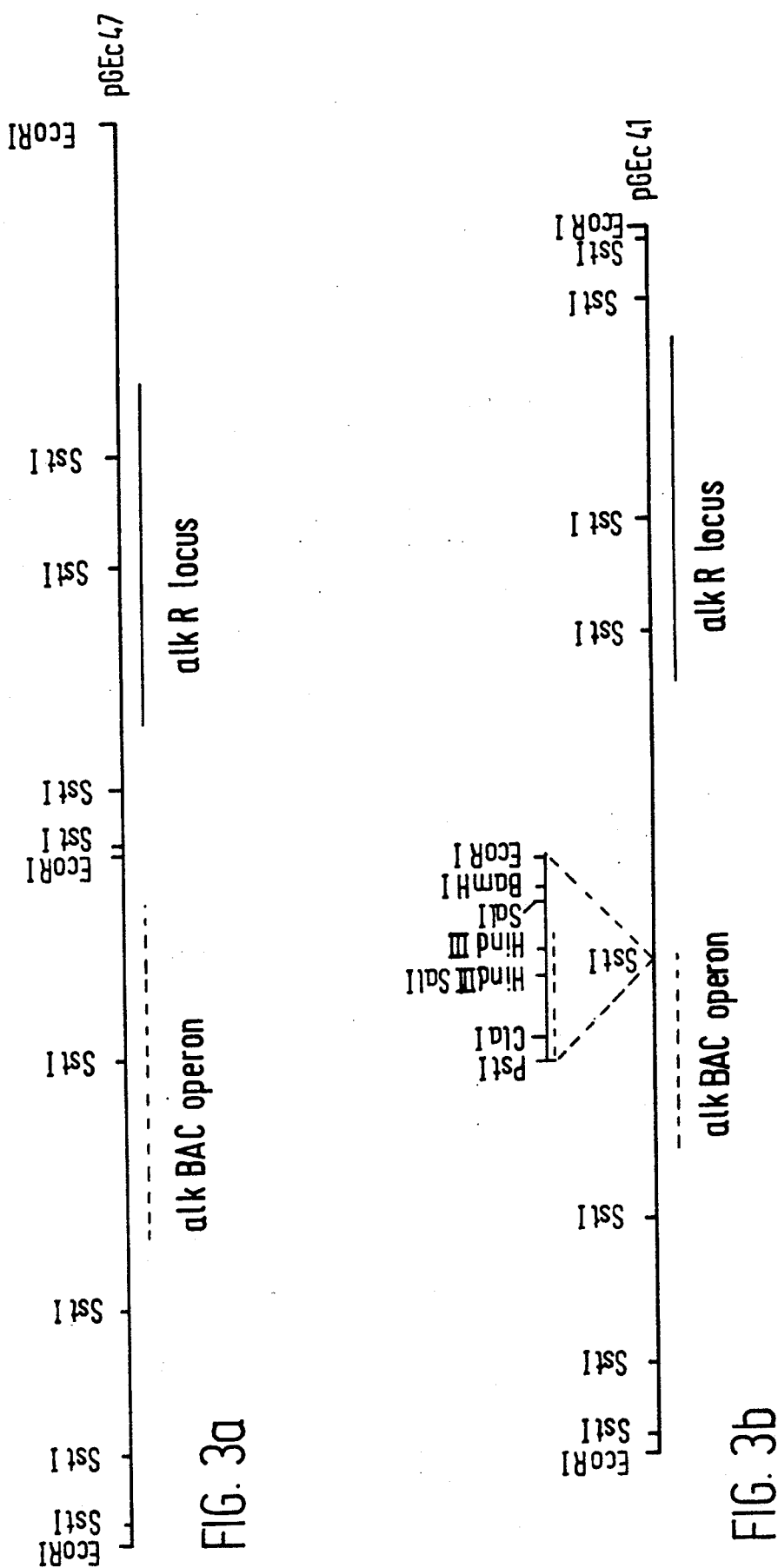
FIG. 3a shows the restriction chart of the insert in pGEc47, which insert contains the alkBAC operon and the alkR locus.

FIG. 3b shows the restriction chart of the insert in pGEc41, which insert consists of the EcoRI fragments A and B with a deletion of 5 kb in the alkBAC operon. The restriction sites lost with this deletion are shown in the figure. To this effect the EcoRI site belongs between the two fragments. The deletion extends to the downstream are of the alkBAC operon, where it terminates between the SstI and PstI sites in the 12.0 and 12.2 positions. The deletion only comprises a small portion (from 0.1 to 0.5 kb) of fragment B, so that the alkR locus has remained outside the deletion. By growth experiments, *inter alia* with the PpS81 strain, which has a mutation in the chromosomally encoded alkanol dehydrogenase, it was shown that the deletion concerned the plasmidic alkanol dehydrogenase gene: whereas the GPp-10 (PpS-81.pGEc47) strain grew as quickly on octane as did GPp-9 (PpG-1.pGEc41), it was found that the GPp-11 (PpS-81.pGEc41) strain grew very poorly on octane.

TABLE A

| | Bacterial strains | | |
|---|---|---|---|
| Strain | source | genotype | plasmid |
| *P. oleovorans* GPo-1 | ATCC 29347 | alk BAC/R | OCT |
| GPo-12 | GPo-1 | — | — |
| GPo-16 | GPo-12 | alk BA/R | pGEc 41 |
| PpG-1 | Nieder (***) | — | — |
| GPp-9 | PpG-1 | alk BA/R | pGEc 41 |
| PpS-81 | Benson (*) | alc A 81 | — |
| GPp-11 | PpS-81 | alk BA/R | pGEc 41 |
| *E. coli* HB-101 | Boyer (**) | | |

(*) S. A. Benson. "Alkane utilization in *Pseudomonas putida*", Ph.D. Thesis University of Chicago 1978.
(**) H. B. Boyer and D. Roulland-Ducroix, J. Mol. Biol. 41 (1969), 459-472
(***) M. Nieder and J. Shapiro, J. Bacteriol. 122 (1975), 93-98

TABLE B

| Growth on octane, tested on plates with octane vapour. | |
|---|---|
| Source | growth |
| GPo-1 | +++ |
| GPo-12 | — |
| GPo-16 | + |
| GPp-9 | ++ |
| GPp-11 | ± |

TABLE C

| Recombinant plasmids from pLAFRI and alk sequences | | |
|---|---|---|
| plasmid | insert(s) | relevant properties |
| pGEc 29 | EcoRI fragment A (16.9 kb) | complementation of AlkA7, alkB201, alkB205, alkB874, alkBA1151 and alkC173 mutations (1) |
| pGEc 40 | EcoRI fragment B (18 kb) | complementation of alkR192, alkR184, alkR256 and alkR252 mutations (1) |
| pGEc 47 | EcoRI fragments A and B | |
| pGEc 41 | EcoRI fragments A and B with a deletion of 5 kb | alkBA/alkR |

(1): M. Fennewald, phD thesis University of Chicago 1979 a. Optimum process conditions

To determine optimum process conditions for alkane hydroxylation and alkene epoxidation, optima for the growth of *P. oleovorans* were determined in mixtures of E* medium and alkanes or alkenes in stirred tank reactors with a working volume of 1 l.

*P. oleovorans* was pre-cultured overnight on E* medium with octane. The main cultures were inoculated to a cell density of 0.1 mg cell dry weight/ml aqueous phase at 450 nm, as described by B. Witholt (Witholt B, J.Bacteriol 109 (1972), 350-364). From the resulting growth curves, the growth rate was determined. The total volume of aqueous phase and organic phase was always 700 ml.

The following optima were determined:

pH: The growth of *P. oleovorans* on n-alkanes is possible between values of 5 and 9. The pH optimum ranges between pH 6.8 and 7.0.

Temperature: *P. oleovorans* can grow on n-alkanes at temperatures below 37° C., with a clear optimum at about 30° C.

Stirring rates: stirring rates in small fermentors turn out to be optimal for growth between 500 and 1000 rpm.

Fraction organic phase: when varying the % (v/v) alkane relative to the total reaction volume, it was found that *P. oleovorans* can grow on 0.5-99% organic phase without the culture being appreciably damaged.

b. Production of 1-octanol and epoxy-octane by recombinant strains

For the production of 1-octanol from n-octane and 1,2-epoxyoctane from octene by the engineered strains, these were cultured on E* medium with pyruvate as the source of carbon and energy. The strains were inocculated from E* plates on 5 ml L medium and pre-cultured on it at 30° C. for 8 hours in the presence of tetracycline.

Subsequently they were transferred to 50 ml E* medium containing 1% (w/v) pyruvate and tetracycline in 250 ml Erlenmeyers and cultured overnight on a shaking plate at 200 rpm and 30° C. The next day they were transferred to E* medium and 20% (v/v) organic phase in fermentors to a cell density of 0.1-0.2 mg cell dry weight/ml aqueous phase. The total end volume was 700 ml, of which 140 ml was organic phase (octane or octene) and 560 ml aqueous phase.

Under conditions found to be optimal for the growth on alkanes, i.e. pH 7.0 (controlled with 2N KOH and 2N $H_2SO_4$) and a temperature of 30° C., stirring rate 700 rpm and oxygen pressure above 50% air saturation, the production by genetically engineered strains was determined both during growth on pyruvate and during the following stationary phase as a result of nitrogen limitation. The product concentrations in the organic phase were measured. The production is given as the specific activity of the cell culture in FIG. 4 in $\mu$mol product formed/ minute/g dry cell mass. This specific activity is high for the strains tested but decreases rapidly during the exponential-growth phase and the stationary phase.

It is found that this marked decrease in production can be partly accounted for by product inhibition, which can be largely prevented by adding a second organic phase which collects the product formed (1-octanol) from the aqueous phase more efficiently. Cyclohexane, cyclohexanol and diesters of phthalates are found to be suitable for this purpose. Dibutyl phthalate, in particular, gives a twice higher end product concentration.

The epoxidation of octene by these strains, however, remains low, probably as a result of a reduced resistance of the engineered strain to the organic phase.

Figure 4A:
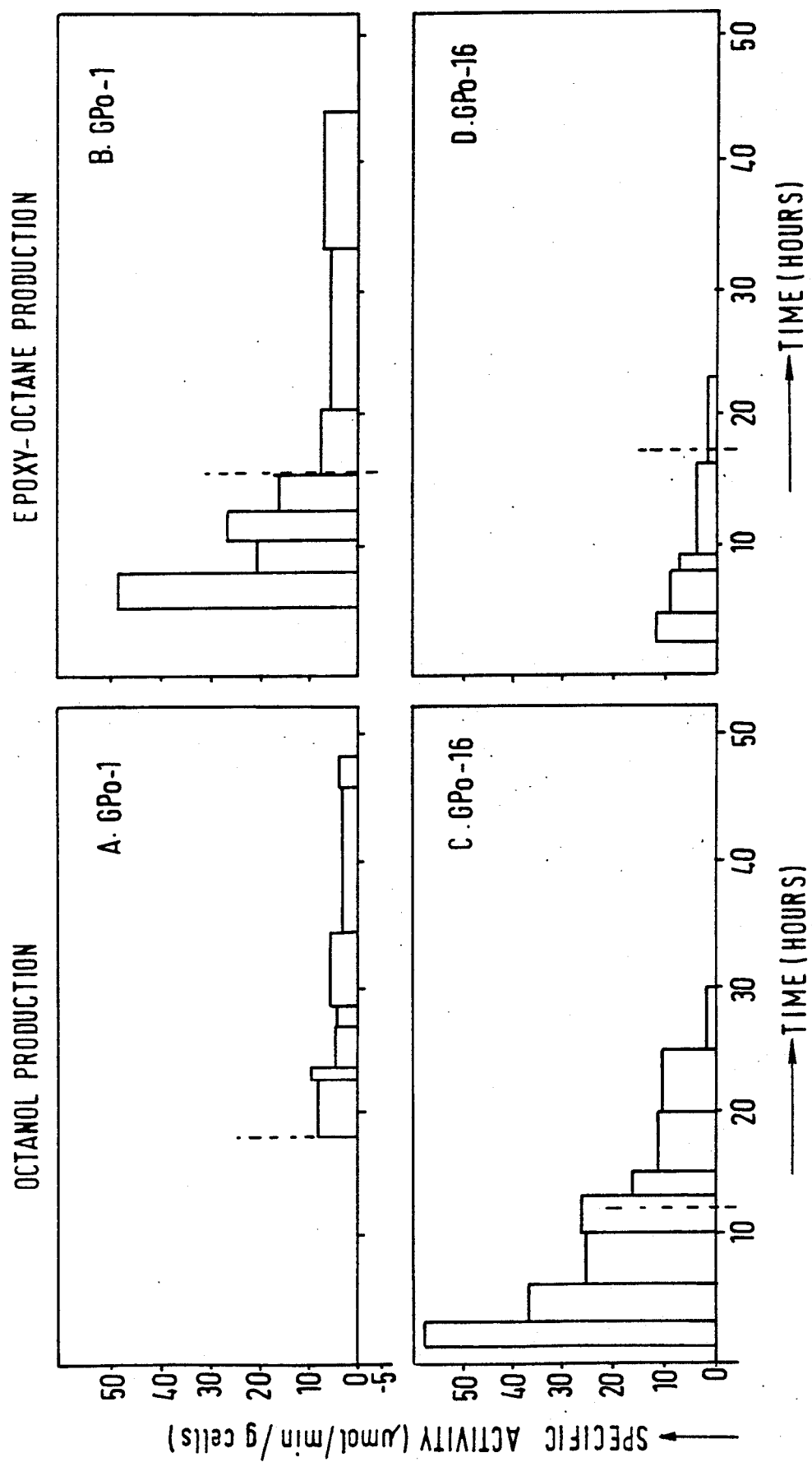
Figure 4B:
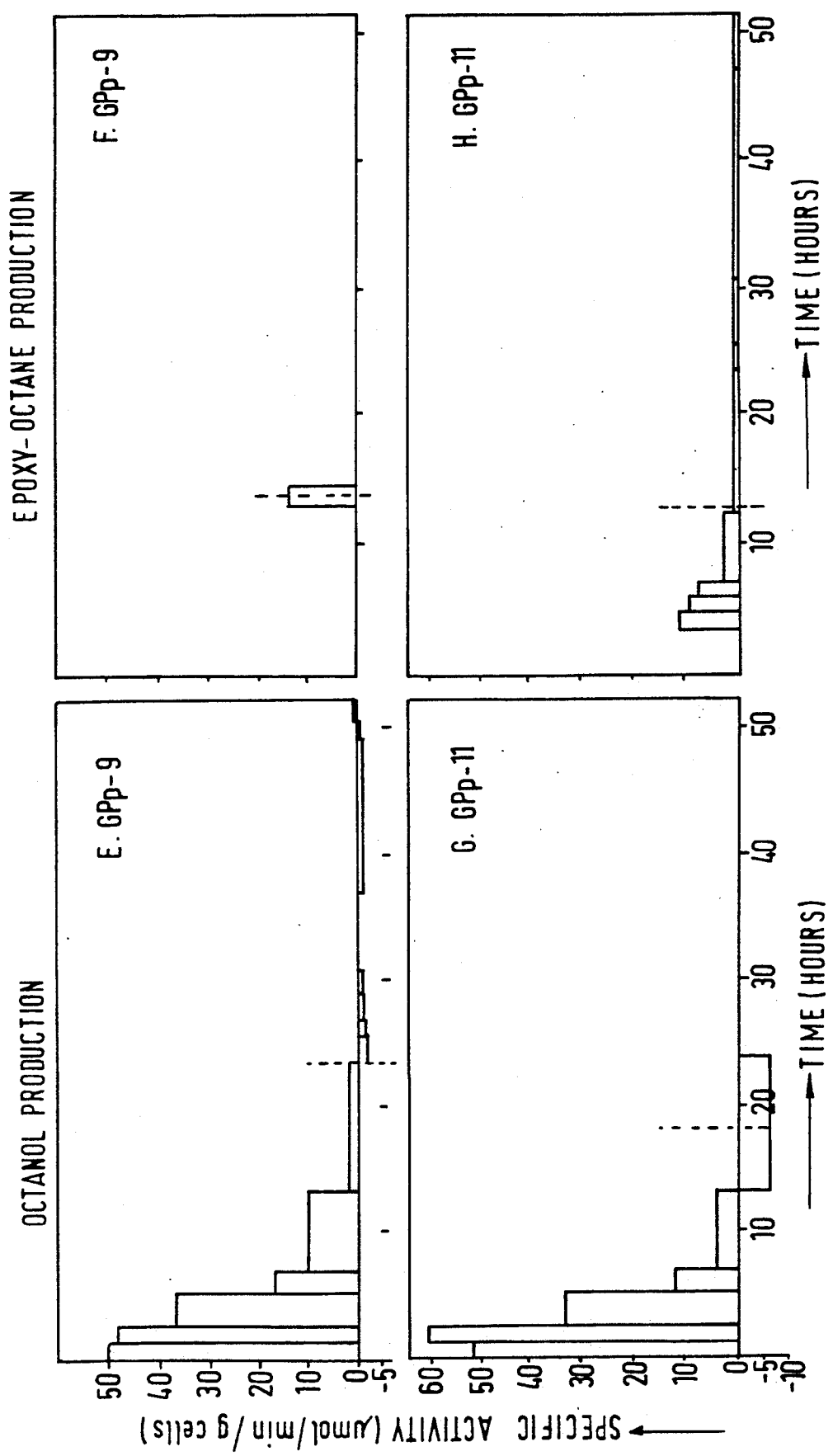

FIG. 4 (parts a and b) shows the production of octanol and 1,2-epoxyoctane of the strains tested as the specific activity of the cell culture in $\mu$mol product per minute per gram dry cell mass. The dotted lines indicate the transition to the stationary phase.

What we claim:

1. A process for producing oxidation products containing a terminal hydroxyl or epoxy group using a microorganism of the genus Pseudomonas having an alkane-hydroxylase enzyme system and genetically engineered to have an absence of an active plasmid encoded alkanol dehydrogenase, said microorganism performing a terminal oxidation of an aliphatic substrate or aliphatic side chain of a substrate of said enzyme system in an aqueous nutrient medium containing a bulk non-aqueous phase under aerobic conditions and avoiding further oxidation of said oxidation products by said alkanol dehydrogenase, said microorganism being resistant to the presence of said non-aqueous phase, said process comprising the steps of culturing said microorganism in said nutrient medium and recovering the oxidation products formed.

2. A process as claimed in claim 1 wherein said substrate is selected from the group consisting of n-alkanes, n-alkenes, n-alkadienes and mixtures thereof containing 6-12 carbon atoms.

3. A process as claimed in claim 1 wherein said microorganism is selected from the species *Pseudomonas oleovorans* or the species *Pseudomonas putida*.

4. A process as claimed in claim 1, wherein said microorganism is a *Pseudomonas oleovorans* strain in which at least the plasmid encoded alkanol-dehydrogenase gene has been removed or inactivated.

5. A process as claimed in claim 1, wherein said microorganism is a *Pseudomonas oleovorans* strain whose natural plasmid has been replaced by a plasmid which contains the alkBA/R genes coding for the alkane-hydroxylase system and which does not contain a gene coding for an active alkanol-dehydrogenase enzyme.

6. A process as claimed in claim 1, wherein said microorganism is a *Pseudomonas oleovorans* strain whose natural plasmid has been replaced by the plasmid pGEc41.

7. A process as claimed in claim 1, wherein said microorganism is cultured at a temperature of 20°-34° C. in a system comprising two liquid phases whose pH is 5-9.

8. A process as claimed in claim 1, wherein said reactor contents are stirred at a stirring rate of 500-1000 rpm.

9. A process as claimed in claim 1, wherein said nutrient medium contains a carbon source selected from the group consisting of pyruvate, citrate and glucose.

10. A process as claimed in claim 1 wherein said non-aqueous phase comprises an organic phase in which the oxidation products are soluble.

11. A process as claimed in claim 10 wherein said organic phase is dibutyl phthalate, cyclohexane, cyclohexanol or mixtures thereof.

12. A process as claimed in claim 1, wherein said microorganism is cultured at a temperature of 20°-34° C. in a system comprising two liquid phases whose pH is 6.8 to 7.0.

* * * * *